United States Patent
Xie et al.

(10) Patent No.: US 8,287,889 B2
(45) Date of Patent: Oct. 16, 2012

(54) FREEZE-DRIED LECITHIN NANOMETER POWDER INJECTION OF URSOLIC ACID AND ITS PREPARATION METHOD

(75) Inventors: Jun Ming Xie, Habei (CN); Yan Bai, Habei (CN); YiMu Yi, Habei (CN); Guang Yang, Habei (CN); ChangGong Zhang, Habei (CN)

(73) Assignee: Wuhan Liyuanheng Pharmaceutical Technology Ltd., Wuhan, Hubei (CN)

( * ) Notice: Subject to any disclaimer, the term of this patent is extended or adjusted under 35 U.S.C. 154(b) by 1568 days.

(21) Appl. No.: 10/535,955

(22) PCT Filed: Nov. 17, 2003

(86) PCT No.: PCT/CN03/00969
§ 371 (c)(1),
(2), (4) Date: May 20, 2005

(87) PCT Pub. No.: WO2004/045619
PCT Pub. Date: Jun. 3, 2004

(65) Prior Publication Data
US 2006/0034933 A1    Feb. 16, 2006

(30) Foreign Application Priority Data
Nov. 21, 2002 (CN) .................................. 02 1 47711

(51) Int. Cl.
*A61K 9/00* (2006.01)

(52) U.S. Cl. ..................................................... 424/400

(58) Field of Classification Search .................... None
See application file for complete search history.

(56) References Cited

U.S. PATENT DOCUMENTS
6,261,607 B1 * 7/2001 Newmark et al. ............. 424/727

FOREIGN PATENT DOCUMENTS
CN        1410066 A * 4/2003

OTHER PUBLICATIONS

CN1410066A English abstract, Apr. 2003.*
English translation of CN 1410066A, Feb. 2010.*

* cited by examiner

*Primary Examiner* — Paul Dickinson
(74) *Attorney, Agent, or Firm* — Hamre, Schumann, Mueller & Larson, P.C.

(57) ABSTRACT

The invention discloses a freeze-dried nanometer powder injection of ursolic acid and a preparing method thereof. It major composes of active material of ursolic acid, complex vehicle of nanometer powder, excipient of freeze-drying. Compared to other popular preparations, its advantages are high target application of liver, concentrate on the affects, increase curative effect, decrease side effect, high dispersity and stability. It is prepared through dissolving ursolic acid as active raw material in medical organic solvent, adding complex vehicle of bean lecithin and stearic acid, stirring while heating until reaction completed, adding distilled water, adding excipient, stirring while heating until reaction completed, filtering with microporous membrane and freeze-drying the filtrate. Its average particle size is 209.5 mm, drug loading is 25.2%. it is for inhibiting and treating liver cancer, decreasing expression of p53, bcl-2 and topo-II.

1 Claim, 1 Drawing Sheet

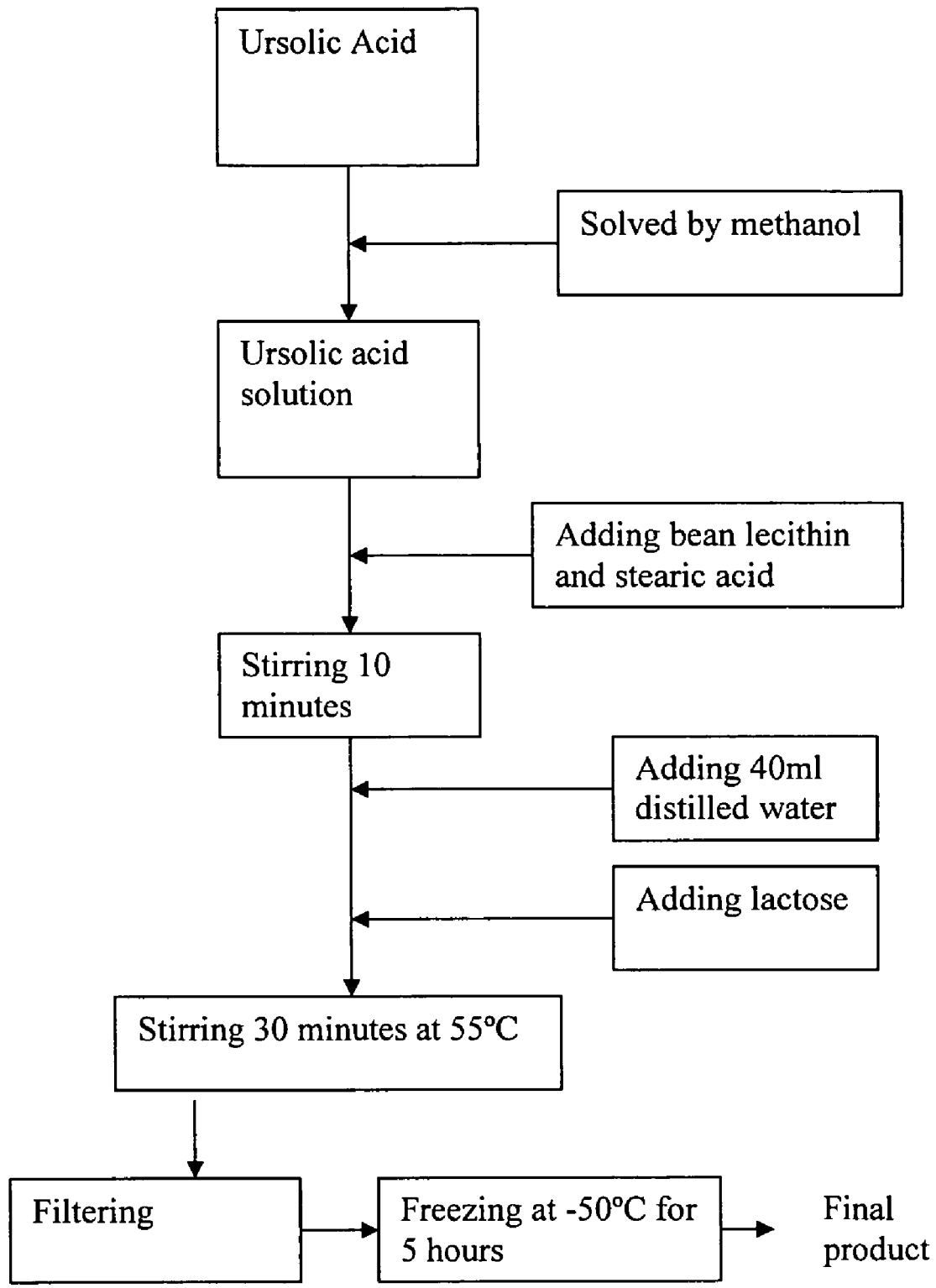

FREEZE-DRIED LECITHIN NANOMETER POWDER INJECTION OF URSOLIC ACID AND ITS PREPARATION METHOD

BACKGROUND OF THE PRESENT INVENTION

1. Field of Invention

The present invention relates to ursolic acid medicine, and more particularly, relates to freeze-dried ursolic acid nano-powder for injection as the preparation method thereof.

2. Description of Related Arts

Ursolic acid is a kind of organic acid, which could be widely found in a variety of plants. It is recently proved that the ursolic acid is effective for inhibiting cancers, inflammations, and some sorts of genes in therapeutic applications.

Nowadays, the pharmacological action of the ursolic acid is still limited on the researching stage. That is to say, there is no mature and effective pharmaceutical formation had been unveiled into the market. In China, some researchers had applied a patent application about the ursolic acid medicine which could be formed in tablet, capsule, injection, oral liquid and so on, the application could be indexed with an application No. 99126892-X. Unfortunately, the water solubility of such ursolic acid was far from satisfaction for most users. With such poor water solubility, it was rather difficult to be absorbed by human body. In short, the application of the ursolic acid was only concentrated on normal raw form of such acid, there is no nanometer scale ursolic acid had been referred or introduced internationally.

SUMMARY OF THE PRESENT INVENTION

A primary object of the present invention is to provide freeze-dried ursolic acid nano-powder for injection and its preparation method so as to enhance the safety of such medicine in applications.

Accordingly, to achieve the above mentioned object, the present invention provides a freeze-dried ursolic acid nano-powder for injection, wherein the nano-powder comprises active raw ursolic acid, nana-powder composite support for carrying the ursolic acid, freeze-dried accessories, wherein the composite support is selected from a group consisting of bean lecithin and stearic acid, the excipient agent of the freeze-dried accessories is selected from a group consisting of mannitol, lactose for injection, glucose for injection, dextran, sodium chloride, sodium glycine, sodium dihydrogenphosphate, union acetic acid and so on.

In comparison with normal formation of the ursolic acid, the ursolic acid nano-powder for injection has liver-targeting effect, and shown strong slow-release effects so as to facilitate its concentration on pathologic area, and ultimately enhance the treating effects, and more importantly, lower the side effects to a great extent.

Furthermore, the present invention provides a manufacturing method for preparing above mentioned freeze-dried ursolic acid nano-powder for injection, comprising the following steps:

a. solving an ursolic acid with an organic solvent;

b. adding composite support, which is selected from lecithin and steraric acid, into organically solved ursolic acid to form a solution;

c. heating the solution within a temperature range between 45° C. to 55° C. with stirring until the reaction is completed;

d. adding excipient agent and distilled water into the solution;

e. heating the solution within a temperature range between 35° C. to 45° C. with stirring until the reaction is completed;

f. filtering the solution via a Millipore membrane; and g. freeze-drying the solution to obtain freeze-dried nano-powder of ursolic acid for injection.

Here, the organic solvent is selected from a group consisting of methanol, and acetone. It is proven that such nano-powder for injection has higher dispersing degree, and a desirable stability. The average particle diameter of such nano-powder is 209.5 mm, and the drug loading is 20.53%. It is demonstrated that the product of the present invention could effectively inhibit and kill liver cancer cells and lower the expression of p53, bcl-2 and Topo-II.

These and other objectives, features, and advantages of the present invention will become apparent from the following detailed description, the accompanying drawings, and the appended claims.

BRIEF DESCRIPTION OF THE DRAWINGS

FIG. 1 is a schematic diagram illustrating the manufacturing process of the freeze-dried ursolic acid nano-powder for injection according to the preferred embodiment of the present invention.

DETAILED DESCRIPTION OF THE PREFERRED EMBODIMENT

Referring to FIG. 1, the manufacturing process of the freeze-dried ursolic acid nano-powder for injection according to the preferred embodiment of the present invention is illustrated. Preferably, the weight ratio of the active raw ursolic acid, nano-particle composite support bean lecithin and stearic acid for carrying the ursolic acid, and the freeze-dried accessories lactose is 0.1-10:0.3-30: 0-10:0.1-20.

According to the preferred embodiment of the present invention, 10 ml methanol is added into 2000 mg ursolic acid to form a solution, wherein the solution is stirred up until the raw ursolic acid is thoroughly solved. Afterwards, 3000 mg lecithin and 1000 mg stearic acid are added into the solution with heating in a temperature range 45-55° C. and continuous stirring process, for example stirring 10 minutes at 505° C. And then, 40 ml distilled water and 2000 mg lactose are added into the solution to be heated to a temperature 35-55° C. and stirred up to 30 minutes. Finally, the solution is screened by a 0.8μ. Millipore membrane to obtain a filtered solution, which is freeze-dried at a temperature range between −55° C. to −50° C. for 2-4 hours to ultimately obtain the final product of the present invention.

Quality Analysis

After a quality analysis, the freeze-dried lecithin ursolic acid nano-powder for injection prepared by the method of the present invention showed an enveloping rate 88.3% and drug loading 25.2%. And the Malven HPPS (high performance particle sizer) tested the average diameter of such nano-powder was 209.5, the zeta potential showed −31.67 mV, and the polydispersity was 0.149.

The Acute Toxic Test Experimented on Animal 1. animal: a group of health Kunming mice was fetched, weighting from 18-20 g, half male and half female. The mice were provided by Medical school of Tongji University and with a batch No. 19-052.

2. the preparation of administered medicine: 2-1, the preparation of ursolic acid: 6660 mg of ursolic acid was added into 10 ml 20% propylene glycol. 2-2, the preparation of the lecithin ursolic acid nano-powder for injection: 8350 mg of sampled ursolic acid nano-powder of the present invention was added into the 10 ml water, wherein each treatment group is administered with a gradually increased dosage of 70% increasing rate.

3. the experiment method: the experimented animals were randomly divided into five groups, each of which has 10 mice, being fasted 14 hours, afterwards, each mouse was is intravenously injected with experimental medicine and the administered mice was intensely observed for treating effects. Commonly, the lethality of the mice was regarded as positive index. After the death mice of each group were recorded and calculated and a $LD_{50}$ value was calculated according to the Bliss statistical method.

4. result analysis: it was recorded that the death of the mice were inclusively occurred within the first two days of observation period. No further death happened to the survival mice after conducting a continuous seven-days observation. It was seen that the death mice shown the symptoms such as tetraparesis, muscular weakness until finally failed to breathe.

FIG. 1 $LD_{50}$ of Ursolic Acid for Injection

| Administering dosage | Animal quantity (n) | Death number (r) | Lethal rate(%) | Dose logarithm (x) | Probability unit (y) |
|---|---|---|---|---|---|
| 2250 | 10 | 0 | 0 | 3.35 | 0 |
| 3713 | 10 | 1 | 10 | 3.57 | 3.72 |
| 6126 | 10 | 3 | 30 | 3.79 | 4.48 |
| 10108 | 10 | 6 | 60 | 4.00 | 5.25 |
| 16678 | 10 | 10 | 100 | 4.22 | 8.09 |

$LD_{50}$ = 7413(mg/kg)

FIG. 2 $LD_{50}$ of PLA(poly lactic acid) -Ursolic Acid nano-powder for Injection

| Administering dosage | Animal quantity (n) | Death number (r) | Lethal rate(%) | Dose logarithm (x) | Probability unit (y) |
|---|---|---|---|---|---|
| 2500 | 10 | 0 | 0 | 3.39 | 0 |
| 4250 | 10 | 2 | 20 | 3.63 | 4.16 |
| 7225 | 10 | 4 | 40 | 3.86 | 4.75 |
| 12283 | 10 | 8 | 80 | 4.09 | 5.86 |
| 20880 | 10 | 10 | 100 | 4.32 | 8.09 |

$LD_{50}$ = 7812(mg/kg)

The above results indicated that the toxicity of the ursolic acid nano-powder for injection was less harmful in comparison with raw ursolic acid.

Pharmacodynamic Experiment

Study of lecithin ursolic acid nano-powder for injection applied for inhibating liver cancer cells.

1. Cell Strain

Cell strain SMMC-7721 of human liver cancer was provided by the biological researching laboratory of the fourth military medical university.

2. Primary Reagents

The culture medium RPMI-1640 was GIBCO cell culture products, which was prepared by 3. distilled water, 10% (V/V) FBS (fetal bovine serum), 1000 u/ml penicillin and 100 u/ml streptomycin, sterilized by 0.22 u filter and refrigerated at 4° C.; the FBS is provided by calf application institution of Jinhua, zhejiang province; MTT [3-(4,5-dimethydiazol-2-yl)-2,5 diphenyl Tetrazolium Bromid] was of SIGMA products, which was prepared by Phosphate buffered saline (PBS, 0.01 mol/L, pH7.4) to form 5 mg/mL solution, sterilized by filter, and refrigerated at 4° C.; TUNEL in situ end labeling reagent TdT (Terminal-deoxylnucleotidyl-Transferase was provided by Promega Co.; DIG-dUTP was of BM products of Germany. Etoposide vepesid was provided by Beijing medicine industry researching insistution; Immunohistachemical Kits was of Wuhan boster Co.

products, wherein the primary antibody was dispatched from imported products, and the second antibody and DAB kit were made in Wuhan.

3. Experiment Method

Preparation of experimental medicine: the lecithin ursolic acid nano-powder for injection was added into water for forming a water solution, afterwards, the solution was boiled (100° C., 30 minutes) so as to adjust the ursolic acid concentration to a 100 mg/mL level. It was noted that the solution should be diluted into desirable concentrations under a sterilized circumstance according to the gradient dilution method.

Cell cultivation: human cancer cell strain SMMC-7721 was conventionally cultured in RPMI-1640 complete culture solution, and was set in 37° C., 5% $CO_2$ culture chamber, passage once in two-three days. Here, the cells of exponential phase of growth were selected for experiments.

Observation of the curable effects of the lecithin ursolic acid nano-powder for injection applied for inhibiting SMMC-7721: the SMMC-7721 of exponential phase of growth was chosen for conventional digestion, the cell concentration was adjusted to $1*10^4$/mL, inoculated at a 96-well tissue culture plate, each well was 100 μL sized; moreover, the lecithin ursolic acid nano-powder for injection and Etoposide vepesid ($VP_{16}$) were diluted with RPMI-1640 culture solution respectively to form differently concentrated solutions for applications; after the cells had been inoculated 24 hours, the solutions were dripped into the culture plate, 100 μL/per well. The experimental control was set with lecithin ursolic acid nano-powder for injection plus SMMC-7721, the positive control was set with $VP_{16}$+SMMC-7721, the negative control was set with CM+SMMC-7721, wherein each control was set with three multititer wells, and Zero-moving wells were 100 μL/well stuffed with complete culture solution. The cells are continuously cultured at 37° C., 5% $CO_2$ culture chamber respectively 1 day, 3 days, 5 days and 7 days, 5 mg/mL MTT are added, 150l/well, after 4 hours of culturing, the supernatant was removed, and then the DMSO (dimethyl sulfoxide) was added into the culture plate, 150 μL/per well. Afterwards, a stirring process was followed to facilitate the solving; the optical density of each well was detected at 490 nm wave length position to obtain the testing result. Finally, a testing curve was drawn wherein the medicine concentration was coordinated as X-axis while the inhabitation rate of cells was coordinated as y-axis. Here, the inhibition rate (E)= $(1-OD_{medicine}/OD_{control})*100\%$.

The therapeutic effects towards p53, TopoII and bcl-2: conventional cell was seeded onto the plate, 24 hours later, the lecithin ursolic acid nano-powder for injection solution of 10 μg/mL was added into the plate to complete a reaction 48-72 hours. On the other hand, another seeded plate was set for contrasting the effect. After the culturing process, the plate was rinsed by ice PBS twice. After then, the plate was pre-cooled with 95% alcohol, and preserved at 4° C. temperature. A transparent glass cement was employed for adhering the back side of the cell plate to a slide, wherein the cell is upwardly oriented, and such slide was dried at a 37° C. temperature, soaked in PBS for 5 minutes, 0.3% Tritonx-100, 10 min, 0.01 mol/L PBS 2*5 min, 3% oxigened water at 37° C. 30 min, PBS rinsed for 3*5 min, added second antibody 37° C. 30 min, rinsed PBS 3*5 min, added with DAB stocked stain 15 μL/per well. The color development would be happened within 5-15 minutes (DAB 5 mg was solved in 10 mL, PBS, filtered with tissue and added with 10 μL-15 μL 30% oxygenized water); Then the plate was observed by a microscope, and the glass slide was disposed into distilled water to terminate the color development. It was indicated that Bcl-2 plate was non-nucleus stained. Moreover, Mayer's Hemotoxylin was applied for sheet-staining 1 minute, and then rinsed by flushing water, hydrochloric alcohol 2-5 minutes, and water, diluted ammonia water 15-20 minutes; after all slides were dehydrated by gradient alcohol, dimethyl benzene was added for 15 minutes, and finally the slides were sealed. The result analysis: after observation by optical microscope, cell nucleus stained with yellow color or brown-yellow color were regard as positive cells by p53 or Topo II, and cell nucleus stained with light yellow color were regarded was negative cells by bcl-2. There clear portions with identified background and strong contrast degree were chosen by low power lens, and the quantities of positive cells of every five hundred cells were calculated by high power lens. The average quantity of positive cells of three portions were set as positive rate, wherein the weak positive rate (+): <20%; strong positive rate (+++): >70%; medium positive rate (++): 20%-70%.

4. Result lecithin ursolic acid nano-powder for injection for dosage-dependently inhibiting liver cancer cells SMMC-7721.

The inhibition towards SMMC-7721 of the lecithin ursolic acid nono-powder for injection was tested by MIT method. It is demonstrated that the lecithin ursolic nano-powder for injection had strong inhibiting and curable effects towards SMMC-7721 cell. As the dosage of such nano-powder for injection was increased, the inhibiting effects was strengthened as well, wherein the inhibiting effects and the dosage was proportionally related (r=0.976, p<0.01). After statistical procedure, wherein the curve line was straighten and regressed to generate a result, the $IC_{50}$ was obtained with 4μ/mL; $IC_{50}$ for nano-powder ursolic acid for injection had a value less than $IC_{50vp16}$, (t=-10.84, p<0.01), illustrating the inhibiting effects of such nano-powder was much better than that of $VP_{16}$.

The influence of the lecithin ursolic acid nano-powder for injection applied to SMMC-7721 cell expression p53, Topo II, and bcl-2.

As shown in FIG. 2, p53, Topo II and bcl-2 expression protein were detected existing within cell nucleus, not in cytoplasm according to immunohistochemical method. The cells were stained with yellow or brown-yellow color. The bcl-2 protein is light-yellow colored within the cytoplasm only. All of three expressions were showed strong positive or positive in SMMC-7721 contrast staining process. It was noted that according to the curable time extended, the reaction would be gradually weakened.

The influence of the lecithin ursolic acid nano-powder for injection applied to SMMC-7721 cell expression p53, Topo II, and bcl-2.

| group | Bcl-2 | P53 | Topo II |
| --- | --- | --- | --- |
| Contrast group | +++ | ++ | ++ |
| 48 h group | ++ | + | ++ |
| 72 h group | + | + | + |

5. Conclusion

The above experiment demonstrated that the lecithin ursolic acid nano-powder for injection was effectively inhibiting human liver cancer cells SMMC-7721, and considered as a better choice compared with Etoposide vepesid $VP_{16}$. More importantly, the inhibiting capability of the medicine could be proportionally enhanced with the administered dosage. Furthermore, the experiment also indicated that such nano-powder ursolic acid could inhibiting the expression of p53, bcl-2, and Topo II, so as to further inhibit the growth of cancer cell.

The raw ursolic acid and the ursolic acid nano-powder for injection were respectively experimented for in vitro treating intestinal cancer cell (HT-29), lung cancer cell (A549), and liver cancer cell (Hep-$G_2$). The relation between administering period and curable effect was intensely observed. That is to say, the inhibiting rate would be recorded according to different administering time of the medicine, such as 2, 3, 4 days administration. It is discovered that administered raw medicine of low concentration, such as 0.1 μg, 0.5 μg, 2 μg/ml, had weak inhibiting effects towards three different cancer cells. As the administering period is extended, the inhibiting effect would gradually be strengthened. On the other hand, the administered medicine of high concentration, such as 10, 50 μg/ml, showed strong inhibiting effect, and as the administering period was extended, the inhibiting effect could increase substantially, peaking 95% at the third day of administration. What is more, the administered nano-powder of the present invention of low concentration, such as 0.1 μg, 0.5 μg, 2 μg/ml, also showed weak inhibiting effect. The extension of administering period could not promptly increase the inhibiting effect. Instead, the administered medicine of 10 μg/ml showed strong inhibiting effect, and the prolonged administering period could abruptly enhance the inhibiting effect. It was noted that for A549, the administered medicine showed relatively weaker inhibiting effect. In short, for HT-29, A549, and Hep-$G_2$, the maximum inhibiting effect occurred mostly at the fourth administering day, therefore illustrating a better slow-release effect of such medicine.

One skilled in the art will understand that the embodiment of the present invention as shown in the drawings and described above is exemplary only and not intended to be limiting.

It will thus be seen that the objects of the present invention have been fully and effectively accomplished. Its embodiments have been shown and described for the purposes of illustrating the functional and structural principles of the present invention and is subject to change without departure form such principles. Therefore, this invention includes all modifications encompassed within the spirit and scope of the following claims.

The invention claimed is:

1. A freeze-dried ursolic acid nano-powder for injection, including a predetermined amount of raw ursolic acid, nano-particle composite support for carrying said raw ursolic acid, and freeze-dried accessories as accessories additives for freeze drying said raw ursolic acid, wherein said nano-particle composite support comprises a predetermined amount of bean lecithin and a predetermined amount of stearic acid, wherein a weight ratio of said raw ursolic acid, said nano-particle composite bean lecithin, said stearic acid, and said freeze-dried accessories is 0.1-10:0.3-30: 0-10:0.1-20;

wherein said freeze-dried accessories comprises an excipient agent selected from a group consisting of mannitol, lactose for injection, sodium glycine, sodium dihydrogenphosphate, and amino acetic acid;

wherein an average diameter of said nano-powder is 209.5 mm, wherein an enveloping rate of said nano-powder is 88.3%, and a drug loading of said nano-powder is 25.2%, wherein a zeta potential of said nano-powder is −31.67 mV.

* * * * *